United States Patent [19]

Levy et al.

[11] Patent Number: 5,679,112
[45] Date of Patent: Oct. 21, 1997

[54] CALCIFICATION-RESISTANT MATERIALS AND METHODS OF MAKING SAME THROUGH USE OF MULTIVALENT CATIONS

[75] Inventors: Robert J. Levy, Ann Arbor, Mich.; Amnon Sintov, Omer, Israel

[73] Assignee: The Board of Regents of the University of Michigan, Ann Arbor, Mich.

[21] Appl. No.: 345,658

[22] Filed: Nov. 28, 1994

Related U.S. Application Data

[63] Continuation of Ser. No. 689,652, Apr. 23, 1991, Pat. No. 5,368,608, which is a continuation-in-part of Ser. No. 515,484, Apr. 30, 1990, abandoned, which is a continuation-in-part of Ser. No. 176,789, Apr. 1, 1988, Pat. No. 5,094,661.

[51] Int. Cl.$^6$ .................. C14H 3/00; A61F 2/02
[52] U.S. Cl. .................. 8/94.11; 8/94.18; 8/94.19; 8/94.28; 623/1; 623/2; 623/3; 623/11; 623/12; 623/66
[58] Field of Search .................. 8/94.11, 94.19, 8/94.18, 94.28; 623/1-3, 11, 12, 66

[56] References Cited

U.S. PATENT DOCUMENTS

| | | | |
|---|---|---|---|
| 714,433 | 11/1902 | Amend | 8/94.29 |
| 725,648 | 4/1903 | Amend | 8/94.29 |
| 2,750,251 | 6/1956 | Bloch et al. | 8/94.11 |
| 2,970,031 | 1/1961 | Nagy | 8/94.29 |
| 3,560,141 | 2/1971 | Kurilla | 8/94.11 |
| 4,097,234 | 6/1978 | Sohde et al. | 8/94.19 |
| 4,378,224 | 3/1983 | Nimni et al. | 8/94.11 |
| 4,481,009 | 11/1984 | Nashef | 8/94.11 |
| 4,729,139 | 3/1988 | Nashef | 8/94.11 |
| 4,753,652 | 6/1988 | Langer et al. | 623/1 |
| 4,770,665 | 9/1988 | Nashef | 8/94.11 |
| 4,786,287 | 11/1988 | Nashef | 8/94.21 |
| 5,002,566 | 3/1991 | Carpentier et al. | 623/2 |
| 5,094,661 | 3/1992 | Levy et al. | 8/94.11 |
| 5,368,608 | 11/1994 | Levy et al. | 8/94.11 |

*Primary Examiner*—Glenn A. Caldarola
*Assistant Examiner*—In Suk Bullock
*Attorney, Agent, or Firm*—Rohm & Monsanto

[57] ABSTRACT

Bioprosthetic materials, either natural or synthetic, are treated with trivalent iron cations, or salts, to prevent in vivo calcification. Such bioprosthetic materials include porcine aortic valve leaflets, bovine pericardium, aortic homografts, biocompatible elastomers, and the like which are intended for invasive, or in-dwelling use in a human or animal body. Simple incubation of the natural bioprosthetic materials in an iron ion-containing solution, such as aqueous $FeCl_3$, particularly with the addition of an anticalcification agent, such as a diphosphonate, prior to implantation has been found to inhibit calcification of the biomaterial over a prolonged period, and to do so without adverse side effects. Incorporation of an iron-containing compound, with or without an additional anticalcification agent, into the formulation for polymers, such as polyurethane, has also been found to inhibit calcification with no adverse side effects.

24 Claims, 1 Drawing Sheet

CALCIFICATION-RESISTANT MATERIALS AND METHODS OF MAKING SAME THROUGH USE OF MULTIVALENT CATIONS

RELATIONSHIP TO OTHER APPLICATION

This invention is a continuation of application Ser. No. 07/689,652, filed Apr. 23, 1991, now U.S. Pat. No. 5,368,608, issued on Nov. 29, 1994, as a continuation-in-part of application Ser. No. 07/515,484, filed on Apr. 30, 1990, now abandoned, as a continuation-in-part of application Ser. No. 07/176,789, filed on Apr. 1, 1988, now U.S. Pat. No. 5,094,661, issued on Mar. 10, 1992, all of the foregoing applications being assigned to the assignee hereof.

STATEMENT OF GOVERNMENT RIGHTS

This invention was made with government support under Contract 5-R01-HL38118 awarded by the National Heart, Lung, and Blood Institute within the National Institutes of Health. The government has certain rights to the invention.

BACKGROUND OF THE INVENTION

This invention relates generally to materials which are resistant to in vivo calcification, and more particularly, to calcification-resistant biomaterial implants comprising synthetic polymers or materials of natural origin, such as bovine pericardium, porcine heart valves or homografts, incorporated with multivalent metallic cations as anticalcification agents.

The life expectancy of patients with severe cardiac valve disease is limited. Valve replacement surgery is often the only means of treating the problem. However, at the present time, there are no replacements for diseased heart valves which are totally problem-free. Currently used replacement valves include mechanical valves which may be composed entirely of a synthetic polymeric material such as polyurethane; bioprosthetic valves derived from glutaraldehyde-pretreated bovine pericardium or porcine aortic valves; and aortic homografts.

Use of mechanical valves is frequently complicated by thrombosis and tissue overgrowth leading to valvular failure. Calcification, however, has emerged as the most frequent cause of the clinical failure of bioprosthetic heart valves fabricated from porcine aortic valves or bovine pericardium. Human aortic homograft implants have also been observed to undergo pathologic calcification involving both the valvular tissue as well as the adjacent aortic wall albeit at a slower rate than the bioprosthetic heart valves. Pathologic calcification leading to valvular failure, in such forms as stenosis and/or regurgitation, necessitates re-implantation. Therefore, the use of bioprosthetic heart valves and homografts has been limited because such tissue is subject to calcification. Pathologic calcification also complicates the use of synthetic vascular grafts and other artificial heart devices, such as pacemakers, because it effects the flexibility of the synthetic polymers used to produce the synthetic devices.

Bioprosthetic heart valves from glutaraldehyde-pretreated bovine pericardium or porcine aortic valves provide blood flow characteristics which closely approximate the natural physiologic. Moreover, use of bioprostheses is accompanied by low incidence of thrombosis, and hence, does not require the administration of anticoagulants. Thus, bioprostheses are the replacement valves of choice, particularly for active children and adolescents. Unfortunately, while calcification of bioprostheses has caused valve failure in patients of all ages, there is a greater incidence of such valve failure in children and young adults. Over 50% of all reported valve implants placed in children under the age of 15 years at the time of initial implantation result in bioprosthesis failure due to calcification within 5 years. In comparison, porcine aortic valve bioprostheses implanted in adults have about a 20% incidence of failure due to calcification after 10 years of implantation. Efforts to provide long term inhibition of calcification have been unsuccessful to date. Currently, the problem of calcification-induced valve failure has prevented the widespread use of bioprosthetic heart valves, even in those patients who could benefit significantly therefrom.

Research on the inhibition of calcification of bioprosthetic tissue has focussed on tissue pretreatment with either detergents or diphosphonates. Both of the aforementioned compounds tend to wash out of the bioprosthetic tissue with time due to blood-material interactions. Thus, these treatments merely delay the onset of the inevitable calcification process. To date, long-term prevention of calcification has been an unattainable result. Accordingly, there is a need for a long-term anticalcification agent for incorporation into bioprosthetic heart valves and other implantable, or in-dwelling, devices which are subject to in vivo pathologic calcification.

The mechanism for pathological calcification of cardiovascular tissue is not understood. Generally, the term "pathologic calcification" refers to the deposition of calcium phosphate mineral salts in association with a disease process. Calcification may be due to host factors, implant factors, and extraneous factors such as mechanical stress. There is some evidence to suggest that deposits of calcium are related to devitalized cells, especially membrane cells, where the calcium pump ($Ca^{+2}$-$Mg^{+2}$-ATPase) responsible for maintaining low intracellular calcium levels is no longer functioning. Calcification has been observed to begin with an accumulation of calcium and phosphorous, present as hydroxyapatite, which develops into nodules which can eventually lead to valvular failure.

We have discovered that the presence of certain multivalent metallic cations, such as trivalent aluminum or ferric cations, prevent in vivo calcification of biomaterials. There are no known examples in the prior art of the use of aluminum or iron salts to inhibit calcification of biomaterials.

Although aluminum is one of the most abundant elements occurring in nature, it plays no biologic role in human physiology. Aluminum has been used for medicinal purposes for many years and can be found in antacids, antiperspirants, acne medications, antidiarrheals, and products used to treat insect bites and stings. Such aluminum-containing products show no toxicity when applied topically; however, high doses of antacids have been known to cause metabolic disturbances, including gastrointestinal absorption of aluminum. Aluminum toxicity, including severe dementia and osteomalacia, has been observed in patients receiving long term hemodialysis. Osteomalacia has been found to correlate with ineffective calcium phosphate mineral deposition in the bones and an increased level of $Al^{+3}$ in the bones. Additionally, the trivalent cation of aluminum ($Al^{+3}$), found in trace amounts in intravenous fluid preparations, has been associated with altered bone mineralization and osteomalacia in patients, such as premature infants, receiving intravenous therapy.

Iron, of course, plays an essential role in biological processes. Iron is found in hemoglobin, the oxygen-carrying molecule of red blood cells in vertebrates, and myoglobin, a hemoglobin-like protein pigment occurring in muscles, for example. Therefore, iron is relatively non-toxic to humans.

It is therefore an object of the invention to provide biomaterials for implantation in a human or animal body which have increased resistance to in vivo pathologic calcification.

It is another object of the invention to provide biomaterials for implantation in a human or animal body which have a long-term, or prolonged, resistance to pathologic calcification.

It is further object of the invention to provide biomaterials for implantation in a human or animal body which exhibit localized calcification inhibition due to anticalcification agents incorporated therein, and thereby avoid the toxic side effects of the anticalcification agents, such as trivalent aluminum, which can result in growth retardation and calcium imbalance from the dosage level required for systemic administration.

It is yet another object of the invention to provide a method of fabricating and/or treating biomaterials for implantation in a human or animal body to render the biomaterials resistant to in vivo pathologic calcification.

It is still a further object of the invention to provide a method of treating tissues of natural origin, such as bioprosthetic heart valves fabricated from bovine pericardium or porcine aortic leaflets, and aortic homografts, which have long-term resistance to pathologic calcification and a reduced risk of valvular failure.

It is yet a further object of the invention to provide a method of making a synthetic organic polymer, such as polyester, polytetrafluoroethylene, polyurethane, nylon or silastic or other silicone-based material, having an anticalcification agent incorporated therein.

SUMMARY OF THE INVENTION

The foregoing and other objects are achieved by this invention which provides, in an implant formed of a biomaterial which is insoluble in the interior of the body of a host living being, an effective amount of a trivalent aluminum salt, or a trivalent ferric salt, for rendering the biomaterial substrate resistant to in vivo pathologic calcification.

In a specific embodiment of the invention, the biomaterial is a tissue which occurs naturally in a donor, which may be a living being. For example, the host and donor beings may be human beings. It is to be understood that the term "living being," particularly as applied herein to a donor being, is intended to include within its scope donor beings which were once alive, such as would be the case with cadaver donors. Additionally, that term includes cultured or engineered tissues, having the characteristics of the tissues of a living being. Thus, the present invention is not limited to tissues obtained from living beings.

In the practice of the present invention, the implant may be installed in a host human being, and the donor being is porcine or bovine. Alternatively, the biomaterial is a synthetic polymer, such as an organic synthetic material, such as polyurethane. In other embodiments, the synthetic polymer is naturally derived, as would be the case with a cellulose or collagen based material.

In accordance with a materials aspect of the invention, a material for implantation in the interior of the body of a living being is characterized by a biomaterial polymeric substance which has incorporated therein an effective amount of trivalent cations, or salts, selected from the group consisting of trivalent aluminum and trivalent iron. The treatment of the material with the trivalent cations renders same calcification-resistant in an in vivo environment.

As discussed hereinabove, the biomaterial polymeric substance is formed, in a specific illustrative embodiment, of a tissue which occurs naturally in a donor living being. Such a substance may be selected from the group of materials consisting of bovine pericardium, porcine heart valve leaflets, saphenous bypass grafts, and aortic homografts.

In other embodiments, the biomaterial polymeric substance is glutaraldehyde-pretreated, and it may be a naturally-derived polymer, such as cellulose. Alternatively, it may be a synthetic polymer, such as one or more of polydimethylsiloxane, polyurethane, ethylene vinyl acetate, polymethyl methacrylate, polyamide, polycarbonate, polyester, polyethylene, polypropylene, polystyrene, polyvinyl chloride, polytetrafluoroethylene, polysulfone, and cellulose acetate.

In accordance with a method aspect of the invention, a material for implantation in the body of a living being includes the step of subjecting a biomaterial polymeric material to a solution containing metallic cations selected from the group consisting of trivalent aluminum and trivalent iron, whereby the material is made resistant to calcification in an in vivo environment.

In a specific embodiment of this method aspect of the invention, the solution contains $AlCl_3$ in a concentration range from 0.1 to 0.001M. In a further embodiment, the solution contains $FeCl_3$ in a concentration range from 0.1 to 0.001M.

In a product-by-process aspect of the invention, a material for implanting in the interior of a human or animal living body, the material is prepared by the process of:

(a) dissolving a synthetic polymeric material in an organic solvent;

(b) adding a predetermined amount of a salt of a metallic trivalent cation selected from the group consisting of aluminum and iron, the salt being soluble in the organic solvent, to the dissolved synthetic polymeric material to form a mixture;

(c) forming the mixture in a desired configuration; and (d) curing the mixture.

In accordance with a specific embodiment of this aspect of the invention, the step of forming the mixture into the desired configuration includes the step of casting the mixture into a film. In a further embodiment, the desired configuration is achieved by molding the mixture.

In a further embodiment of this aspect of the invention, the synthetic polymeric material is polyurethane and the organic solvent is dimethyl sulfoxide. Also, the salt of a metallic trivalent cation is selected from the group consisting of aluminum silicate, aluminum oxide, aluminum phosphate, aluminum palmitate, aluminum oleate, aluminum oxalate, aluminum magnesium silicate, aluminum stearate, aluminum diacetate, aluminum hydroxide, aluminum isopropoxide, and aluminum hypophosphite.

In a further method aspect of the invention, a glutaraldehyde pre-treated bioprosthetic tissue is formed by incubating the bioprosthetic tissue in an aqueous solution of $AlCl_3$ ranging from 0.1M to 0.001M for a period of time ranging from approximately between 1 hour to 24 hours at a temperature of approximately between 4° C. to 25° C.

In a still further method aspect, the bioprosthetic tissue is incubated in an aqueous solution selected from the group consisting of $FeCl_3$ ranging from 0.1M to 0.001M and $FeCl_3$ and citrate for a period of time ranging from approximately between 1 hour to 24 hours at a temperature of approximately between 4° C. to 25° C.

BRIEF DESCRIPTION OF THE DRAWING

Comprehension of the invention is facilitated by reading the following detailed description, in conjunction with the annexed drawing, in which.

DETAILED DESCRIPTION

Figure 1:
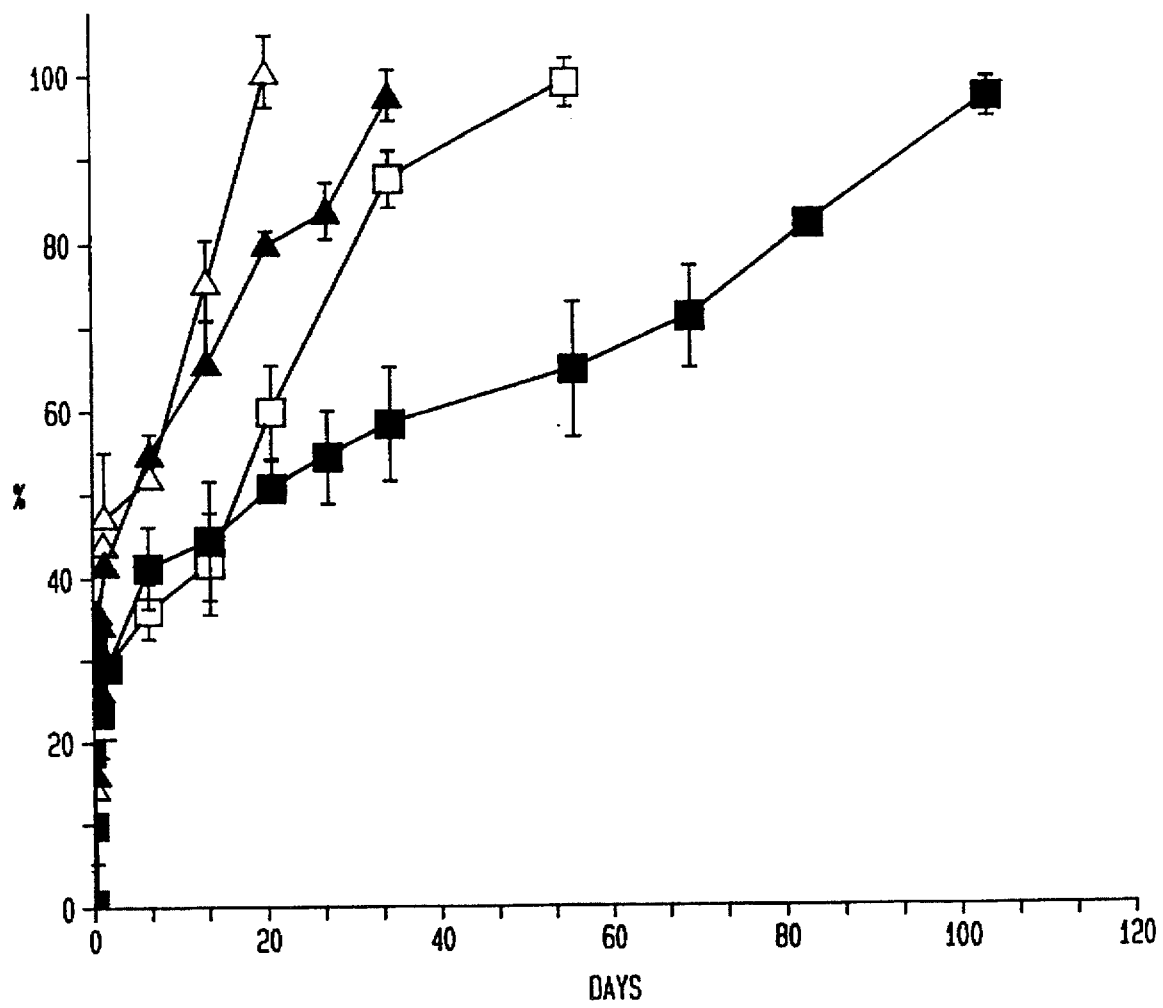
FIG. 1 is a graphic representation of cumulative release of anticalcification agent expressed as a percent (%) of total agent present in a synthetic polymeric matrix versus time expressed as days.

Calcification-resistant materials useful for implantation in a living being can be prepared by various techniques which complex multivalent metallic cations, preferably trivalent aluminum ions or ferric ions, with a biomaterial. The word "complex" is used herein broadly to indicate some form of combination wherein the multivalent cations are bound to, incorporated on, or in, the substrate biomaterial in such a manner as to provide anticalcification effects over a sustained period of time.

The term "biomaterial" as used herein denotes any biocompatible polymeric material which is known, or becomes known, as being suitable for in-dwelling uses in the body of a living being, i.e., it is biologically inert and physiologically acceptable, non-toxic, and insoluble in the environment of use.

Illustrative biocompatible polymeric materials suitable as the biomaterial substrate include naturally-derived polymers, such as cellulose or collagen-based materials, or synthetic polymers, whether hydrophilic or hydrophobic, including, without limitation, polydimethylsiloxane, polyurethane, ethylene vinyl acetate, polymethyl methacrylate, polyamide, polycarbonate, polyester, polyethylene, polypropylene, polystyrene, polyvinyl chloride, polytetrafluoroethylene, polysulfone, or cellulose acetate. It is to be understood that the term polymer is to be construed to include copolymers, such as the copolymer of polyurethane and silicone.

The term biomaterial also specifically includes biologically-based "bioprosthetic tissues" such as bovine pericardium, porcine valve leaflets, and homographic tissues, such as aortic homografts, and saphenous bypass grafts.

Given below are several specific illustrative techniques for producing calcification-resistant materials in accordance with the principles of the invention. Although the examples given are primarily directed to the preparation of calcification-resistant heart valves components, the techniques described herein are applicable to the creation of any other device, prothesis or implant comprising biomaterials of the type used for in-dwelling or surgically implanted devices. In its broadest sense, the calcification-resistant materials can be configured to encompass, inter alia, knit or woven fabrics, single or plural filaments, extruded or molded items, coatings on polymeric substrates or biological tissues, etc.

TREATING BIOPROSTHETIC HEART VALVES

Bioprostheses such as porcine aortic valve leaflets or bovine pericardium are typically stabilized and preserved in glutaraldehyde following harvesting, illustratively a 0.2% solution of glutaraldehyde in 0.05M HEPES buffer (N-2-hydroxyethylpiperazine-N'-2-ethanesulfonic acid available from Sigma Chemical Co., St. Louis, Mo.). The glutaraldehyde-preserved bioprostheses can be stored at 4° C. for prolonged periods of time.

In accordance with one embodiment of the invention, glutaraldehyde-treated bioprosthetic tissue is incubated for a period of time, illustratively 24 hours, at a temperature ranging from the storage temperature (4° C.) to room temperature (25° C.) in an aqueous solution of a water-soluble aluminum compound that will ionize in solution to form trivalent aluminum cations. Following incubation, the bioprosthetic tissue is washed thoroughly (10×) with sterile, deionized water and then implanted in the subject.

An aqueous solution is recommended for bioprosthetic tissue inasmuch as organic solvents have deleterious effects on biologically-based tissue and could have toxic effects on the patient once implanted. However, an organic solvent is certainly within the contemplation of the invention. Isopropanol, for example, has been used in connection with bioprosthetic tissues.

Water soluble aluminum salts, include without limitation, aluminum chlorate, aluminum lactate, aluminum potassium sulfate, aluminum sodium sulfate, aluminum sulfate, aluminum nitrate, and aluminum chloride. The examples herein are directed to aluminum chloride ($AlCl_3$). However, other compounds, such as aluminum lactate, would produce the same beneficial results and have a more neutral pH than $AlCl_3$.

In the specific $AlCl_3$ embodiment, a solution of the desired concentration is prepared in a fume hood by adding water to anhydrous $AlCl_3$ (Mallinckrodt, Inc. Pads, Ky.) over an ice bath with constant stirring due to the extremely exothermic nature of the reaction. $AlCl_3$ concentrations from 0.1M to 0.001M have been shown to be effective in the studies reported hereinbelow.

It should be noted that the aluminum chloride solution concentration range is given for purposes of illustration only, and can be varied by those of skill in the art because it is greatly in excess of the therapeutically effective amount. However, the ability to incorporate such a high concentration of trivalent aluminum cations in the bioprosthetic heart valve tissue, thereby placing a high concentration of drug at the potential site of calcification, is a significant advantage of this invention over the prior art.

Although the length of time (i.e., 24 hours) allotted for incubation in the embodiments described hereinabove does not appear to cause deleterious effects to the bioprosthetic tissue, it has been discovered that glutaraldehyde-pretreated bovine pericardium has sufficient $Al^{+3}$ uptake within 1 hour of incubation (at 25° C.) in an $AlCl_3$ solution to render the bioprosthetic tissue resistant to calcification. Table 1 below demonstrates that the additional uptake over a three day period is not significant.

TABLE 1

| Incubation Solution | $Al^{+3}$ Content (nM/mg) | |
|---|---|---|
| | 1 hour | 3 day |
| $10^{-1}$M $AlCl_3$ | 351.4 ± 15.8 | 394.5 ± 48.0 |
| $10^{-2}$M $AlCl_3$ | 96.4 ± 17.4 | 105.3 ± 2.3 |
| $10^{-3}$M $AlCl_3$ | 24.6 ± 4.9 | 40.0 ± 8.8 |

In addition to $Al^{+3}$, the anti-calcification effects of other multivalent metallic cations were investigated. It was discovered that $Fe^{+3}$ is also a useful calcification agent. In certain preferred embodiments, the combination of $Fe^{+3}$ plus citrate or diphosphonate likewise produces anticalcification effects.

In like manner to the $AlCl_3$ embodiments, glutaraldehyde pretreated bovine pericardium pieces (1 cm) were preincubated for 1 hour at 25° C., illustratively in 0.1M solution of $FeCl_3$ (available from Fisher Scientific Co., Fairlawn, N.J.). Among water-soluble ferric salts, preferred for use in the practice of the invention, are ferric chloride, ferric nitrate, ferric bromide, ferric sodium edentate, ferric sulfate, and ferric formate.

TABLE 2

| Incubation Solution | $Fe^{+3}$ Content (nM/mg) | |
| --- | --- | --- |
|  | 1 hour | 24 hours |
| 0.1M $FeCl_3$ | 155.3 ± 36.1 | 147.6 ± 24.1 |

In yet another advantageous embodiment, iron and aluminum salts were combined with a titrate salt, such as sodium citrate (available from J. T. Baker, Inc., Phillipsburg, N.J.) or citric acid. A synergistic effect was produced which was more significant than the effect of either component alone. Citrate is a known $Ca^{+2}$ chelator. Although the mechanism is not understood, the citrate ion may reduce the competition of $Fe^{+3}$ and $Ca^{+2}$, for example, for the same sites on the tissue.

In still another advantageous embodiment, water-soluble diphosphonate salts, such as ethanehydroxydiphosphonate (EHDP) or aminopropanehydroxydiphosphonate, produce a similar remarkable synergistic effect when combined with the multivalent metallic cations described hereinabove. The molar concentrations of $FeCl_3$ and EHDP or citrate which produce anti-calcification effects (0.00001M) are so dilute individually, that per se, they would be unable to produce anti-calcification effects. However, the combination produces surprisingly effective results and mitigates against any toxic effects of the anticalcification agent.

Both the iron and aluminum salts have been found to inhibit calcification by incubation in solutions over the concentration range of 0.00001M to 0.1M. However, molar concentrations for pre-treatment of bovine pericardium tissue for long term effects is preferably between 0.001M to 0.1M, and most preferably between 0.01M and 0.1M.

TREATING HOMOGRAFT TISSUE

Homograft tissue is typically cryopreserved rather than glutaraldehyde-treated. After the tissue is thawed, the homograft tissue is incubated in a sterile $AlCl_3$ solution for a period of time, illustratively an hour, prior to implantation. A shorter period of time is allotted for incubating the still viable homograft tissue than the devitalized bioprosthetic tissue.

PREPARATION OF SYNTHETIC MATERIALS

Trivalent aluminum cations may also be incorporated into synthetic polymers.

A synthetic polymeric substrate material, such as medical grade polyurethane (sold under the trademark Thiomer by Thermedics Corp., Woburn, Mass.) is dissolved in a solvent, such as dimethylacetamide (DMAC) or tetrahydrofuran (THF), to form a clear homogenous solution. An aluminum compound, illustratively dehydrated aluminum silicate, is added to the liquid mixture. The aluminum compound should be chosen for its solubility and compatibility with both the polyurethane and the solvent.

In addition to aluminum silicate, a variety of aluminum compounds can be incorporated into the polymeric substrate material. Other illustrative examples include aluminum oxide, aluminum phosphate, aluminum palmitate, aluminum oleate, aluminum oxalate, aluminum magnesium silicate, aluminum stearate, aluminum diacetate, aluminum hydroxide, aluminum isopropoxide, and aluminum hypophosphite.

In a preferred embodiment, dehydrated aluminum silicate, known as kaolin, produced a satisfactory calcification-resistant polyurethane film. About 10% by weight kaolin in DMAC-dissolved polyurethane was cast into thin polymer films on the order of 200 μm in thickness and dried in a vacuum oven at 55° C. with 2 millitorr pressure. The resulting polyurethane films were uniform, and demonstrated satisfactory elastic properties suitable for heart valve leaflets.

In addition to being cast as a film, the aluminum-containing synthetic polymeric material may be formed, such as by extrusion or compression molding, into a variety of configurations suitable for implantation or any other in-dwelling application where calcification is a risk. For example, the new synthetic polymer can easily be formed into heart valve leaflets, artificial heart device pumping bladders, detachable cardiac balloons, and the like. Of course, the material can also be applied as a coating or film, such as a coating to pacemaker leads.

Of course, the aluminum compound could also be incorporated in the polymeric matrix by other known material engineering techniques, such as by combining it with the polymeric precursors. In the kaolin example given, combination of kaolin with the polyurethane precursors assures its presence as the diisocyanate-polyether reaction goes to completion. Thus, kaolin is introduced as a primary ingredient in the solid phase polymerization.

One of the significant advantages of incorporating aluminum into the polymeric matrix is that it enables release of the anticalcification agent at a controlled rate over an extended period of time.

It is to be understood, however, that ferric salts may also be incorporated into synthetic polymers. Illustrative, ferric salts which are soluble in an organic solvent, such as dimethyl acetamide, include ferric nitrate and ferric acetate. In particular, ferric nitrate has been successfully incorporated into polyurethanes by a solvent casting technique. Exemplary polyurethanes include polyurethane-mitralthane NPU5 (Symbion, Denver, Co.), Biomer (Ethicon, Somerville, N.J.), and Tecoflex (Thermedics, Woburn, Mass.).

The addition of finely divided and sifted particles of ferric chloride or ferric nitrate to the components of the primary polymerization reaction has successfully incorporated these anticalcification agents into polymer matrices consisting of polydimethyl siloxanes, such as the silastics MDX 44210 and Q7-4840 (both available from Dow Corning, Midland, Mich.).

EXPERIMENTAL

A. Bioprosthetic Tissue in Rat Subdermal Model

Bioprosthetic tissue samples in the form of parietal pericardium from mature cows was obtained at slaughter and immediately placed in a 0.6% solution of glutaraldehyde in 0.05M HEPES buffer. After 24 hours, the tissue samples were transferred to 0.2% glutaraldehyde in HEPES and stored at 4° C. Using a #7 cork borer, the pericardium specimen was cut into 1 cm diameter pieces.

The bioprosthetic tissue was incubated in $AlCl_3$ solutions of various concentrations (0.001M, 0.01M, 0.1M) for 24 hours. The tissue was also incubated in non-aluminum ion containing solutions (pH 3.6 and pH 7.4) as controls. The acid control group was utilized because the pH of the $AlCl_3$ solutions is acidic.

The incubated bovine pericardium samples were implanted in two subcutaneous pouches dissected in the ventral abdominal wall of weanling rats (male, CD, Sprague-Dawley, weighing 50–60 gm). After periods of 21 and 60 days, the tissue samples were removed and examined for calcification by measuring the level of $Ca^{++}$ ions in the tissue. Tables 3 and 4 below summarizes the results where N refers to the number of rats in the treatment group.

Calcification of bioprosthetic tissue samples was markedly inhibited after both 21 day and 60 day implant intervals. More significantly, all concentrations or $Al^{+3}$ appeared to inhibit calcification to the same degree. The $Al^{+3}$ treatment also had no observable adverse effect on rat growth or bone morphology.

Reference to Tables 3 and 4 shows that the tissue calcium levels for the bioprosthetic specimens implanted for both 21 and 60 days was not significantly different. This is indicative that $Al^{+3}$ has the ability to afford long-term inhibition of calcification.

TABLE 3

Tissue $Ca^{++}$ Levels at 21 Days Post-Implant

| Treatment | N | Tissue $Ca^{++}$ (µg/mg) |
|---|---|---|
| 0.001M $AlCl_3$ | 10 | 3.5 ± 1.8 |
| 0.01M $AlCl_3$ | 10 | 3.5 ± 3.5 |
| 0.10M $AlCl_3$ | 12 | 3.8 ± 0.5 |
| 0.001M HCL (pH 3.6) | 10 | 54.4 ± 10.2 |
| 0.10M HEPES (pH 7.4) | 10 | 44.2 ± 14.7 |

TABLE 4

Tissue $Ca^{++}$ Levels at 60 Days Post-Implant

| Treatment | N | Tissue $Ca^{++}$ (µg/mg) |
|---|---|---|
| 0.10M $AlCl_3$ | 8 | 4.13 ± 1.03 |
| 0.001M HCL (pH 3.6) | 8 | 119.91 ± 19.47 |
| 0.10M HEPES (pH 7.4) | 10 | 143.81 ± 25.49 |

Compared to the two control groups, calcification was markedly inhibited in all groups which were pretreated with $Al^{+3}$-containing solutions. Of particular importance is the fact that this effect occurs even at extremely low concentrations of $AlCl_3$. Moreover, there was no observable adverse effect on calcium metabolism.

Based upon a measured $Al^{+3}$ uptake of approximately 350 nM/mg, an estimate of the total $Al^{+3}$ content of a trileaflet bioprosthetic heart valve (dry weight—approximately 300 mg) would be $10.5 \times 10^4$ nM or 2.8 mg. This total dose is less than the daily intake of 100–568 mg/day reported to be associated with dementia in patients with renal failure on hemodialysis. In patients with normal renal functions, a single 2.8 mg dose of $Al^{+3}$ should be easily eliminated by the kidney. Therefore, $Al^{+3}$ toxicity should be highly unlikely.

The mechanism of $Al^{+3}$ in inhibiting calcification is unknown. However, the trivalent cation should have the ability to form strong ionic bonds with negatively charged phosphate groups, as well as other negatively charged residues, in the collagen fibrils of bioprosthetic tissue, for example. Such ionic bonds could inhibit the formation of calcium phosphate nuclei in the tissue. Bound $Al^{+3}$ may also cause stearic inhibition of calcium deposition. Strong ionic bonds formed between $Al^{+3}$ and negatively charged moieties would provide prolonged inhibition of calcification in contradistinction to the short-lived effects of detergents and diphosphonates.

To demonstrate the effectiveness of $Fe^{+3}$ and $Fe^{+3}$ plus citrate, glutaraldehyde-pretreated bovine pericardium pieces (1 cm) were preincubated for 1 hour at 25° C. in 0.1M solutions of $AlCl_3$, $FeCl_3$, lanthanum trichloride ($LaCl_3$; Alfa Products, Danvers, Mass.),gallium nitrate ($GaNO_3$; Aldrich Chemical Co., Milwaukee, Wis.), $FeCl_3$+citrate, and 0.05M HEPES buffer (control).

Pieces of the treated bovine pericardium were implanted subdermally in weanling male rats (50–60 g) for 21 days or 60 days. At explant, the specimens were analyzed for calcium inhibition by measuring the presence of $Ca^{+2}$ in the tissue. The results are shown below in Table 5 where N indicates the number of rats in the experimental group:

TABLE 5

| Pre-Treating Solution | N | Tissue $Ca^{++}$ (µg/mg) |
|---|---|---|
| 0.1M $AlCl_3$ | 14 | 5.5 ± 0.2 |
| 0.1M $FeCl_3$ | 8 | 13.6 ± 4.6 |
| 0.1M $FeCl_3$ + 0.1M Citrate | 10 | 5.9 ± 1.7 |
| 0.1M $LaCl_3$ | 7 | 50.2 ± 9.6 |
| 0.1M $GaNO_3$ | 10 | 87.4 ± 8.6 |
| 0.05M HEPES (control) | 27 | 63.6 ± 5.7 |

Table 5 shows that $Fe^{+3}$ is also effective anticalcification agent for glutaraldehyde-pretreated bioprosthetic heart valves. Lanthanum and Gallium ions are known to inhibit calcium phosphate crystal formation and to have an affinity for phosphate. However, these ions do not bind well to cell membranes and therefore do not produce the anticalcification effects of aluminum and iron.

None of the rats which received subdermal implants preincubated as described above showed any evidence of toxicity after 21 or 60 days. Moreover, none of the rats exhibited abnormal growth patterns and, histologic examination of distal femoral epiphyses, revealed normal growth plate architecture.

The effectiveness of the combination of $FeCl_3$ and the diphosphonate ethanehydroxy-diphosphonate was demonstrated by incubating glutaraldehyde-pretreated bovine pericardium specimens in solutions of $FeCl_3$, EHDP, and a combination thereof. The treated specimens were implanted in weanling rats as described hereinabove. After 21 days, the bovine pericardium tissue specimens were explanted and analyzed for calcium content. The results are shown below in Table 6.

TABLE 6

| Incubation Solution | $Ca^{+2}$ Content (µM/mg) |
|---|---|
| .05M HEPES (control) | 57.1 ± 12.8 |
| .0001M $FeCl_3$ | 52.7 ± 4.6 |
| .1M EHDP | 109.0 ± 18.5 |
| 0001M $FeCl_3$ + .1M EHDP | 15.4 ± 4.6 |

B. Rat Aortic Homograft Subdermal Studies

Thoracic aortas were removed from mature rats (male, CD, Sprague Dawley, Rattus norvegicus weighing between 200–300 g). The harvested aortas were split to completely expose the lumen and rinsed thoroughly with sterile, normal saline (0.9% NaCl).

The thoracic aortas were washed and incubated in $AlCl_3$ or control solutions, specifically, $AlCl_3$ solutions of the following concentrations: 0.01M; 0.001M; and 0.0001M; an acidic control solution (0.001M HCl, pH 3.0) and a physiologically buffered control solution (0.05M HEPES buffer, pH 7.4).

The aortic homograft samples were implanted in a subcutaneous pocket dissected in the ventral abdominal wall of weanling rats (50–60 g) of the same species. The rats received an injection of the antibiotic, chloramphenicol (100 mg/Kg/24° C.), for three days post-operation to prevent infection of the surgical wound.

The implanted homograft tissue samples were explanted after 21 days and were analyzed for calcium, aluminum, and evidence of morphological changes. Blood samples were obtained at sacrifice and analyzed for serum levels of calcium and aluminum. Bone samples (femurs) were removed from a representative sample of each group and fixed in 10% neutral buffered formalin for bone morphology assessment.

Calcium levels in untreated homografts showed a progressively increasing trend with time post-implant. The aluminum pretreatment inhibited calcification in the subdermal model. Table 7 shows calcium inhibition in homograft tissue samples which were explanted after 21 days. Referring to Table 7, a significant reduction of tissue calcium levels was observed for all $AlCl_3$ concentrations as compared to the controls. Serum calcium levels were not significantly different between $AlCl_3$ and control groups. Rat weight gains in the $AlCl_3$-treated groups and the acid control group were expressed as a percentage of the weight gain shown in the physiologically buffered control group for the 21 day period. None of the groups showed significant growth retardation.

TABLE 7

$Al^{+++}$ Inhibition of Aortic Homograft Calcification
Rat (21 day, Male) Subcutaneous Implants - 3 Week Data*

| GROUP | N | Implant $Ca^{++}$ (μg/mg) | Explant $Ca^{++}$ (μg/mg) | Serum $Ca^{++}$ (mg/dl) | Rat Wt. Gain % of Control |
|---|---|---|---|---|---|
| 0.01M $AlCl_3$ | 5 | 0.80 ± 0.14 | 13.9 ± 4.9 | 12.3 ± 0.4 | 113 |
| 0.001M $AlCl_3$ | 5 | 0.91 ± 0.15 | 36.6 ± 7.1 | 13.6 ± 0.7 | 116 |
| 0.0001M $AlCl_3$ | 5 | 1.4 ± 0.07 | 114.5 ± 14.9 | 11.0 ± 0.4 | 110 |
| 0.001M HCL | 5 | 1.2 ± 0.27 | 159.8 ± 10.6 | 13.0 ± 0.9 | 118 |
| 0.05M HEPES | 5 | 1.2 ± 0.15 | 171.0 ± 13.2 | 13.0 ± 0.6 | 100 |
| UNTREATED UNIMPLANTED | 5 | 0.77 ± 0.10 | — | — | — |

*Data as Mean ± Standard Error

Aluminum levels in the homograft samples were measured prior to implantation and showed a greater concentration of $Al^{+3}$ than at explant. However, the two control groups showed a trend to greater $Al^{+3}$ concentration at explant than at implant. The amount of calcium accumulation was negatively correlated with the amount of $Al^{+3}$ present in the homografts at implant. Table 8 shows the $Al^{+3}$ and $Ca^{+2}$ content of aortic homograft specimens which were explanted after 21 days.

TABLE 8

$Al^{+++}$ Content of Aortic Homografts and Inhibition of Rat (21 day, Male) Subcutaneous Implants (3 wk) Calcification*

| GROUP | N | Explant $Ca^{++}$ (nM/mg) | Implant $Al^{+++}$ (nM/mg) | Explant $Al^{+++}$ (mg/dl) |
|---|---|---|---|---|
| 10 nM/μl $AlCl_3$ | 5 | 346.7 ± 123 | 164.7 ± 4.9 | 65.3 ± 7.5 |
| 1 nM/μl $AlCl_3$ | 5 | 914.5 ± 178 | 49.8 ± 4.4 | 9.79 ± 1.1 |
| 0.1 nM/μl $AlCl_3$ | 5 | 2863 ± 372 | 20.5 ± 1.3 | 5.34 ± 0.30 |
| 1 nM/μl HCL | 5 | 3995 ± 265 | 0.83 ± 0.30 | 5.19 ± 0.56 |
| 50 nM/μl HEPES | 5 | 4275 ± 330 | 1.28 ± 0.72 | 5.67 ± 0.22 |
| UNTREATED UNIMPLANTED | 5 | — | 0.29 ± 0.14 | — |

*Data as Mean ± Standard Error

C. In Vitro and In Vivo Studies of Calcification-Resistant Synthetic Polymeric Systems
(1) In Vitro Studies Calcification-resistant synthetic polymeric materials made in accordance with the present invention were evaluated for in vitro release characteristics. These studies confirm that sustained release of the cationic anticalcification agents of the present invention can be obtained from synthetic polymeric matrix materials.

a. The Specimens

Anticalcification agents in the form of $Al(NO_3)_3$ and $FeCl_3$ were incorporated into Silastic 6605-41 (a silicone-polyurethane copolymer available from Dow Corning, Midland, Mich.) and Biomer® (a polyetherpolyurethane available from Ethicon, Somerville, N.J.) matrices by a solvent casting technique in an mount of approximately 10% by weight. The anticalcification agent and the polymer were separately dissolved in dimethyl acetamide, the resulting solutions were thoroughly mixed together, and films were cast from the mixture and dried under vacuum at 50° C. overnight. The dried films were approximately 0.54±0.03 mm thick.

b. The Studies

In vitro release of the anticalcification agent from the polymer matrices was evaluated by incubating the specimen (1×1×0.5 $cm^3$) at 37° C. under perfect sink conditions in 0.05M HEPES buffer at pH 7.4. At specified time intervals, a small piece of the polymeric matrix specimen was removed, dried under vacuum, and weighed accurately. The $Al^{+3}$ or $Fe^{+3}$ content was determined by neutron activation analysis.

The results of the in vitro release studies of the synthetic polymeric matrices incorporating $Al^{+3}$ and $Fe^{+3}$ are shown in FIG. 1. FIG. 1 is a graphic representation of cumulative release of anticalcification agent expressed as a percent (%) of total agent present in the specified polymeric matrix material over time (days). Data for the calcification-resistant polymeric matrices are indicated on FIG. 1 as follows: □ is 10% $FeCl_3$ in Silastic 6605-41; Δ is 10% $FeCl_3$ in Biomer®, ■ is 10% $Al(NO_3)_3$ in Silastic 6605-41, and ▲ is 10% $Al(NO_3)_3$ in Biomer®.

Referring to FIG. 1, the release kinetic studies show that all formulations exhibit an initial burst phase of release, followed by an exponentially decreasing release rate. The release rate from Biomer® matrices is more rapid than from Silastic 6605-41 matrices. Furthermore, $Fe^{+3}$ cations were completely released more rapidly than $Al^{+3}$ cations from both types of polymeric matrix material. All specimens, however, demonstrated the capacity for sustained release of the anticalcification agents.

Average release rates in vitro over a 21 day period, and the estimated average dose in rats, were calculated based upon the release data shown in FIG. 1. The mean release rates and estimated dosages from the calcification-resistant polymeric matrix specimens are set forth in Table 9. The data, based on a sample (N) of five, indicate that the average doses of $Al^{+3}$ and $Fe^{+3}$ are comparable, irrespective of the polymer matrix type.

TABLE 9

Mean release rates and estimated dosages from polymeric matrices in vitro ($1 \times 1 \times 0.05$ cm$^3$)

| Agent | Polymer | N | Average In Vitro release rate (µg/24 h ± s.d.) | Estimated average dose in rats (µg/kg/24 h) |
|---|---|---|---|---|
| Fe$^{3+}$ | Biomer | 5 | 214.49 ± 41.69 | 857.96 |
|  | Silastic 6605-41 | 5 | 156.59 ± 53.48 | 626.36 |
| Al$^{3+}$ | Biomer | 5 | 178.14 ± 29.72 | 712.56 |
|  | Silastic 6605-41 | 5 | 141.69 ± 9.97 | 566.76 |

(2) In Vivo Studies

Efficacy of the calcification-resistant synthetic polymeric materials of the present invention in vivo was studied by co-implanting specimens of the polymeric materials described hereinabove in part C. (1) with glutaraldehyde-pretreated bovine pericardium for 21 days using a subdermal rat model.

Male rats (CD strain, Charles River, Burlington, Mass.) 21 days old were anaesthetized with an intraperitoneal injection of Ketamine and Rompun®. Subcutaneous pouches were created over the anterior abdominal wall, pieces of glutaraldehyde-pretreated bovine pericardium (1×1 cm) were implanted in these pouches, either as isolated control implants or as co-implants with calcification-resistant polymeric matrices (1×1 cm$^2$) or specimens of the polymeric matrix material cast as a film (1×1 cm$^2$) but containing no anticalcification agent. After 21 days, the rats were killed by CO$_2$ asphyxiation and the glutaraldehyde-pretreated bovine pericardium pieces were explanted, lyophilized and hydrolysed in 6N HCl. Calcium (Ca$^{+2}$) levels in the glutaraldehyde-pretreated bovine pericardium pieces were determined in aliquots of the hydrolysates by atomic absorption spectroscopy.

Results of the in vivo evaluation of the calcification-resistant synthetic polymeric implants are shown in Table 10. Table 10 shows the total Ca$^{+2}$ levels in the explanted glutaraldehyde-pretreated bovine pericardium pieces after 21 days implantation and the % calcification of the explanted glutaraldehyde-pretreated bovine pericardium pieces compared to the isolated control implant.

TABLE 10

Controlled release calcification inhibition: results of glutaraldehyde-pretreated bovine pericardium (GPBP) subdermal implant studies in rats

| Cocipient | Polymer | N | Calcium levels in explanted GPBP pg/mg of dried tissue | % Calcification in the explanted GPBP compared to control |
|---|---|---|---|---|
| FeCl$_3$ | 6605-41 | 10 | 14.25 ± 2.91 | 19.26* |
| FeCl$_3$ | Biomer | 10 | 44.67 ± 8.04 | 60.38 |
| Al(NO$_3$)$_3$ | 6605-41 | 10 | 14.28 ± 5.78 | 17.87 |
| Al(NO$_3$)$_3$ | Biomer | 10 | 31.04 ± 5.48 | 38.85 |
| No drug | 6605-41 | 30 | 52.27 ± 9.35 | 74.70 |
| No drug | Biomer | 20 | 64.20 ± 10.24 | 91.16 |
| Control GPBP | None | 40 | 69.97 ± 10.76 | 100.00 |

*P < 0.001.

Both $Al^{+3}$ and $Fe^{+3}$ exhibit significant inhibition of calcification (P<0.001) when incorporated in Silastic 6605-41 matrices. When compared with control values, greater than 80% calcification inhibition occurred. $Al^{+3}$ incorporated into Biomer® matrices also produced significant calcification inhibition. None of the rats appeared to sustain any adverse effects on somatic growth or bone development due to the presence of the controlled-release matrix material.

Thus, it is apparent that the calcification-resistant synthetic polymeric materials of the present invention would be useful, for example, as replacement heart valves. Not only is the polymeric material resistant to in vivo calcification, but its presence can impart anticalcification agent to biological tissue in the vicinity of the implant.

The foregoing examples and experimental results were given for the purpose of illustration only and are not to be construed as limiting the scope of the invention. Numerous and varied examples of the application of the principles of the invention can be devised by those of skill in the art without departing from the spirit and scope of the invention. Moreover, the examples cited do not preclude the use of other techniques for complexing trivalent aluminum cations with substrate biomaterial to achieve the goal of long-term incorporation of anti-calcification agents in implant materials.

The calcification-resistant material is ideally suited for any body-invasive uses in which pathologic calcification is a possibility. Such uses include, vascular grafts, pacemakers, numerous other prosthetic or implanted devices, such as artificial bone and hip joints, cosmetic implants of silicone, tendon protheses, etc.

What is claimed is:

1. An implant formed of a biocompatible biomaterial which is a tissue which occurs naturally in a donor living being and is insoluble in the interior of the body of a host living being, said biomaterial having incorporated therein an effective amount of trivalent iron cations and at least one anticalcification agent selected from the group consisting of citrates and diphosphonates to render said biomaterial resistant to in vivo pathologic calcification.

2. The implant of claim 1 wherein said biomaterial is selected from the group consisting of bovine pericardium, porcine heart valve leaflets, saphenous bypass grafts, and aortic homografts.

3. An implant formed of a biocompatible biomaterial which is a biocompatible synthetic polymer and is insoluble in the interior of the body of a host living being, said biomaterial having incorporated therein an effective amount of trivalent iron cations to render said biomaterial resistant to in vivo pathologic calcification.

4. The implant of claim 3 wherein said biocompatible synthetic polymer is an organic synthetic material selected from the group consisting of polydimethylsiloxane, polyurethane, ethylene vinyl acetate, polymethyl methacrylate, polyamide, polycarbonate, polyester, polyethylene, polypropylene, polystyrene, polyvinyl chloride, polytetrafluoroethylene, polysulfone, and cellulose acetate.

5. The implant of claim 4 wherein said organic synthetic material is a polyurethane.

6. A material suitable for implantation in the interior of the body of a living being, the material being a tissue which occurs naturally in a donor living being having incorporated therein an effective amount of trivalent iron cations and at least one anticalcification agent selected from the group consisting of citrates and diphosphonates to render the tissue resistant to pathologic calcification in an in vivo environment.

7. The material of claim 6 wherein said tissue is selected from the group consisting of bovine pericardium, porcine heart valve leaflets, saphenous bypass grafts, and aortic homografts.

8. A material suitable for implantation the interior of the body of a living being, the material being a biocompatible biomaterial which is a biocompatible synthetic polymer having incorporated therein an effective amount of trivalent iron cations to render the biomaterial resistant to pathologic calcification in an in vivo environment.

9. The material of claim 8 wherein the biocompatible synthetic polymer is selected from the group consisting of polydimethylsiloxane, polyurethane, ethylene vinyl acetate, polymethyl methacrylate, polyamide, polycarbonate, polyester, polyethylene, polypropylene, polystyrene, polyvinyl chloride, polytetrafluoroethylene, polysulfone, and cellulose acetate.

10. A material for implanting in the interior of a human or animal living body, the material being prepared by the process of:
    (a) dissolving a biocompatible synthetic polymeric material in an organic solvent;
    (b) adding a soluble salt of trivalent iron cations to the dissolved biocompatible synthetic polymeric material to form a mixture; and
    (c) forming said mixture into a desired configuration.

11. The material for implanting in the interior of a human or animal living body prepared by the process of claim 10 wherein said step of forming said mixture into said desired configuration comprises the step of casting said mixture into a film.

12. The material for implanting in the interior of a human or animal living body prepared by the process of claim 11 further comprising the step of drying the cast film in a vacuum oven at 50° to 55° C.

13. The material for implanting in the interior of a human or animal living body prepared by the process of claim 10 wherein said step of forming said mixture into said desired configuration comprises the step of molding said mixture.

14. The material for implanting in the interior of a human or animal living body prepared by the process of claim 10 wherein said biocompatible synthetic polymeric material is selected from the group consisting of polydimethylsiloxane, polyurethane, ethylene vinyl acetate, polymethyl methacrylate, polyamide, polycarbonate, polyester, polyethylene, polypropylene, polystyrene, polyvinyl chloride, polytetrafluoroethylene, polysulfone, and cellulose acetate.

15. The material for implanting in the interior of a human or animal living body prepared by the process of claim 14 wherein said biocompatible synthetic polymeric material is selected from the group consisting of polyurethanes and polydimethylsiloxanes and copolymers thereof, and said organic solvent is selected from the group consisting of dimethyl sulfoxide, dimethylacetamide, and tetrahydrofuran.

16. The material for implanting in the interior of a human or animal living body prepared by the process of claim 15 wherein said synthetic polymeric material is polyurethane and said organic solvent is dimethyl sulfoxide.

17. The material for implanting in the interior of a human or animal living body prepared by the process of claim 10 wherein said soluble salt of trivalent iron is selected from the group consisting of ferric acetate, ferric chloride, ferric nitrate, ferric bromide, ferric sodium edentate, ferric sulfate, and ferric formate.

18. The material for implanting in the interior of a human or animal living body prepared by the process of claim 10 wherein step (b) further includes adding a soluble anticalcification agent selected from the group consisting of citrates and diphosphonates.

19. The implant of claim 3 having further incorporated therein at least one anticalcification agent.

20. The implant of claim 19 wherein the at least one anticalcification agent is selected from the group consisting of citrates and diphosphonates.

21. The material of claim 8 having further incorporated therein at least one anticalcification agent.

22. The material of claim 21 wherein the at least one anticalcification agent is selected from the group consisting of citrates and diphosphonates.

23. A material for implanting in the interior of a human or animal living body prepared by the process of:
    incubating a glutaraldehyde pre-treated bioprosthetic tissue in an aqueous solution of soluble salt of trivalent iron and an anticalcification agent selected from the group consisting of citrates and diphosphonates, the soluble salt of trivalent iron and the anticalcification agent selected from the group consisting of citrates and diphosphonates having concentrations in the range of from about 0.1M to 0.00001M for a period of time ranging from approximately between 1 hour to 24 hours at a temperature of approximately between 4° C. to 25° C.

24. The material of claim 23 wherein the soluble salt of trivalent iron is selected from the group consisting of ferric acetate, ferric chloride, ferric nitrate, ferric bromide, ferric sodium edentate, ferric sulfate, and ferric formate.

* * * * *